United States Patent [19]

Mohri

[11] Patent Number: 4,765,321
[45] Date of Patent: Aug. 23, 1988

[54] DISPLACEMENT SENSOR FOR A LIVING BODY

[75] Inventor: Kaneo Mohri, Fukuoka, Japan

[73] Assignee: TDK Corporation, Tokyo, Japan

[21] Appl. No.: 931,699

[22] Filed: Nov. 14, 1986

[30] Foreign Application Priority Data

Dec. 27, 1985 [JP] Japan .............................. 60-294650
Feb. 21, 1986 [JP] Japan ............................. 61-24383[U]

[51] Int. Cl.⁴ ............................................. A61B 7/04
[52] U.S. Cl. .................................... 128/715; 381/67; 381/177
[58] Field of Search ................. 128/715, 773, 739; 381/67, 177; 181/158, 160

[56] References Cited

U.S. PATENT DOCUMENTS

| 2,294,015 | 8/1942 | Salb et al. | 128/715 |
| 2,583,941 | 1/1952 | Gordon, Jr. | 128/715 X |
| 3,555,187 | 1/1971 | Rowley | 128/715 |
| 4,072,822 | 2/1978 | Yamada | 381/67 |

FOREIGN PATENT DOCUMENTS

0833737 4/1960 United Kingdom ................. 381/67

OTHER PUBLICATIONS

Sakaguchi et al.; "A New Simple Mechanostimulator with Special Reference to its Physiological Applic."; *IEEE Trans. on Biomed. Eng.*, vol. BME-25, No. 5, 9-1978, pp. 484-486.

Primary Examiner—Kyle L. Howell
Assistant Examiner—Angela D. Sykes
Attorney, Agent, or Firm—Burgess, Ryan & Wayne

[57] ABSTRACT

A displacement sensor for a living body provides an improved stethoscope and/or cardiogram. The apparatus has a diaphragm which is placed on the surface of a living body, a permanent magnet located on the diaphragm, an inductor arrangement located adjacent to the permanent magnet so that the saturable inductor changes its inductance according to movement or vibration of the magnet, a processor circuit which processes the inductance variation in the inductors to provide an electrical output signal for visual display and recording purposes, and a hollow sound tube which introduces an acoustic vibration sound of the diaphragm to the ears of a doctor. The present apparatus provides not only acoustic sound output but also visual display and a printed copy as a mechanocardiogram sensor.

11 Claims, 8 Drawing Sheets

DISPLACEMENT SENSOR FOR A LIVING BODY

BACKGROUND OF THE INVENTION

The present invention relates to a displacement sensor and, in particular, relates to such a device which senses the displacement or vibration of a living body. The present invention is applicable to a stethoscope for medical purposes, and mechanocardiogram.

Conventionally, an acoustic stethoscope has been used for diagnosing a living body. A prior stethoscope places a diaphragm on a surface of a living body, and the vibration of the diaphragm is listened to by a doctor through a stethoscope tube.

Therefore, a prior stethoscope has the disadvantage that only a single doctor can listen to the sound of vibration of heart valves of a living body, but it can not be listened to by a plurality of persons. Further, a prior stethoscope has the disadvantage that a doctor cannot listen to the sound of a heart beat due to a low frequency less than 20 Hz and the output of the stethoscope can not be recorded.

On the other hand, a prior electrocardiogram records pulsation or drive electrical signals of a heart, but it does not record an actual mechanical movement of a heart. Therefore, if there is something wrong with a heart such as valve desease and arteriosclerosis, it could not be detected by a prior electrocardiogram. Conventional mechanocardiograph sensors for detection of heart movement are difficult to treat due to their bad treatability.

SUMMARY OF THE INVENTION

It is an object, therefore, of the present invention to overcome the disadvantages and limitations of a prior displacement sensor by providing a new and improved displacement sensor for a living body.

It is also an object of the present invention to provide a displacement sensor which is used as a stethoscope and/or a cardiogram, which is not only listened to, but also recorded on a paper, and/or displayed on a screen.

The above and other objects are attained by a displacement sensor comprising a diaphragm which is placed on a living body; a magnetic pole fixed on said diaphragm; a pair of inductors positioned close to said magnetic pole; and a processor for processing output signals of said inductors.

Said processor is essentially an astable multivibrator.

Preferably, each of said inductors has a plurality of series connected inductors in a star shape so that the earth magnetism and undesired magnetic noise are cancelled.

BRIEF DESCRIPTION OF THE DRAWINGS

The foregoing and other objects, features, and attendant advantages of the present invention will be appreciated as the same become better understood by means of the following description and accompanying drawings wherein.

DESCRIPTION OF THE PREFERRED EMBODIMENTS

Figure 1:
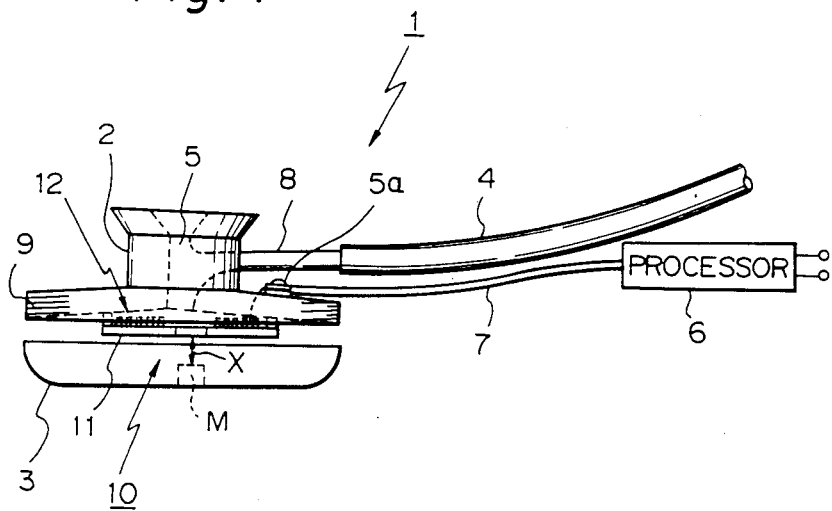
FIG. 1 shows a structure of a displacement sensor according to the present invention.

FIG. 1 shows a structure of a displacement sensor according to the present invention. In the figure, the displacement sensor or the stethoscope 1 has a main body 2, a diaphragm 3 and a sensor 10.

A hollow rigid tube 8 is coupled with the main body 2, and a flexible tube 4 is coupled with said hollow rigid tube 8. Accordingly, an acoustic vibration in empty space 5 in the main body 2 propagates through the rigid tube 8 to the flexible tube 4, the far end of which is to be coupled with an ear of a doctor. The main body 2 has a screw 9 at the outer surface of the same, and the diaphragm 3 is engaged with that screw. The sensor 10 is mounted between the diaphragm 3 and the main body 2.

The sensor 10 functions to generate an electrical signal according to the vibration of the diaphragm 3, and said sensor 10 has a magnetic pole M (a small permanent magnet), a group of inductors 12 which cause inductance variation according to displacement of said magnetic pole M, and a holder 11 for fixing the inductors 12. The sensor terminal 5a is mounted on the main body 2 so that the lead wires of said inductors 12 are coupled with the sensor cable 7 through the sensor terminal 5a. The far end of the sensor cable 7 is coupled with a processor 6 which processes the signal from the sensor 10.

Accordingly, the stethoscope of FIG. 1 functions both for a prior stethoscope which propagates acoustic vibration to an ear, and for an electric stethoscope which provides electrical output information according to vibration of the diaphragm 3.

Figure 2A:
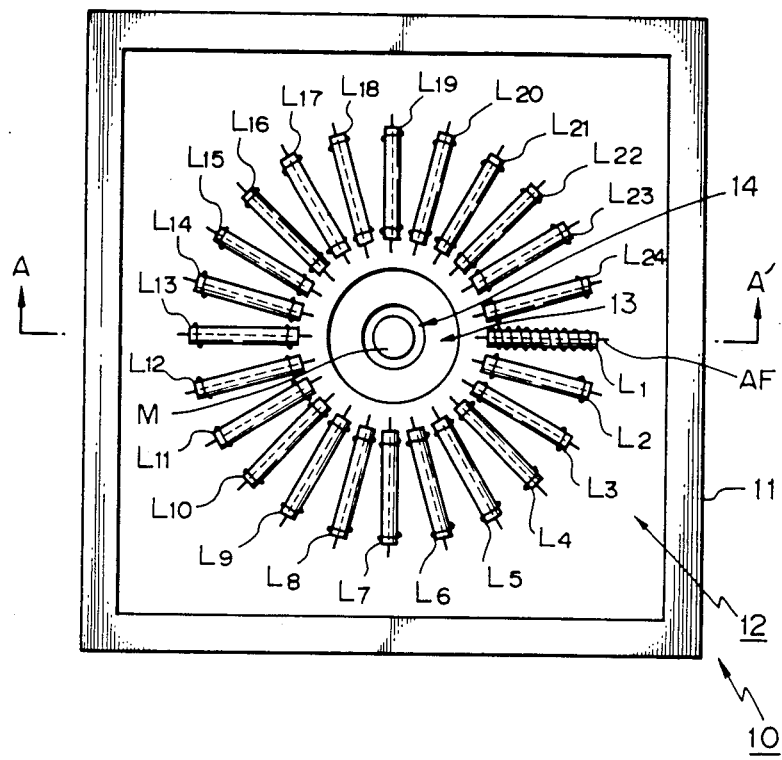
FIG. 2A is a plane view of a sensor of the displacement sensor of FIG. 1.
Figure 2B:
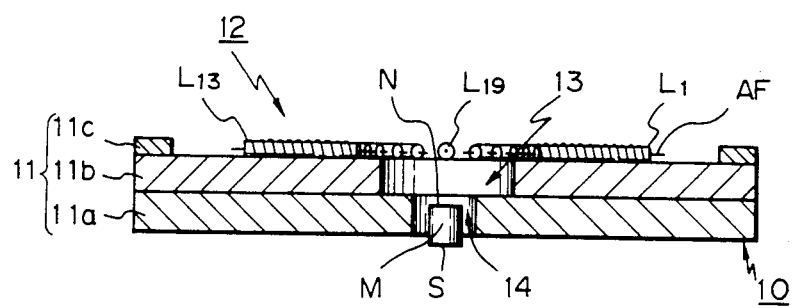
FIG. 2B is a cross section at the line A—A' of FIG. 2A.
Figure 3:
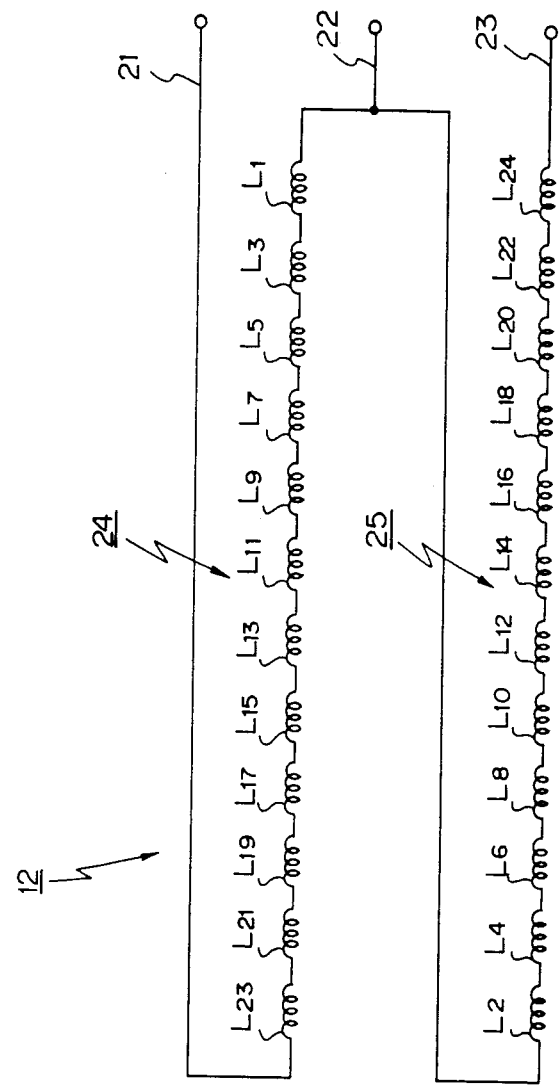
FIG. 3 shows electrical connection of inductors of a sensor of FIG. 2A.

FIG. 2A shows a plane view of the sensor 10, and FIG. 2B shows a cross sectionnal view at the line A—A' of FIG. 2A.

The permanent magnet M mounted on the diaphragm 3 is in the present embodiment a cylindrical permanent magnet with a diameter of 3 mm.

The holder 11 comprises a first insulation member 11a, a second insulation member 11b and a third insulation member 11c, laminated to one another. The first insulation member 11a has a circular hole 14 at the center so that said permanent magnet M is movably inserted in the hole 14. The second insulation member 11b has also a hole 13 which is coplanar with said hole 14. The hole 13 is a little larger than said hole 14. The group of inductors 12 are positioned radially around the hole 13. The third insulation member 11c is located at the periphery of the second member 11b so that the third member 11c provides a room for mounting inductors 12.

Each of saturable inductors 12 ($L_1$ through $L_{24}$) has a core wire AF and a coil wound on said wire AF. The wire AF is, for instance, made of amorphous material (composition is for instance $Co_{68}Fe_4Si_{13}B_{15}$ in atomic percent). The diameter of the wire AF is, for instance, 110 $\mu$m, and the length of the same is 3 mm. The coils are connected in series alternately so that the coils $L_1$, $L_3$, $L_5$, $L_7$, $L_9$, $L_{11}$, $L_{13}$, $L_{15}$, $L_{17}$, $L_{19}$, $L_{21}$, and $L_{23}$ are connected in series, and the coils $L_2$, $L_4$, $L_6$, $L_8$, $L_{10}$, $L_{12}$, $L_{14}$, $L_{16}$, $L_{18}$, $L_{20}$, $L_{22}$, and $L_{24}$ are connected in series. The first inductor group $L_1$ through $L_{23}$ and the second inductor group $L_2$ through $L_{24}$ are also connected in series by connecting one end of the coil $L_1$ to one end of the coil $L_2$. The lead lines 21, 22, 23 for coupling with an external circuit are provided at one end of the coil $L_{23}$, the coupling between the coils $L_1$ and $L_2$, and one end of the coil $L_{24}$, respectively.

The lead lines 21, 22 and 23 are connected to the processor 6 through the sensor cable 7.

Figure 4:
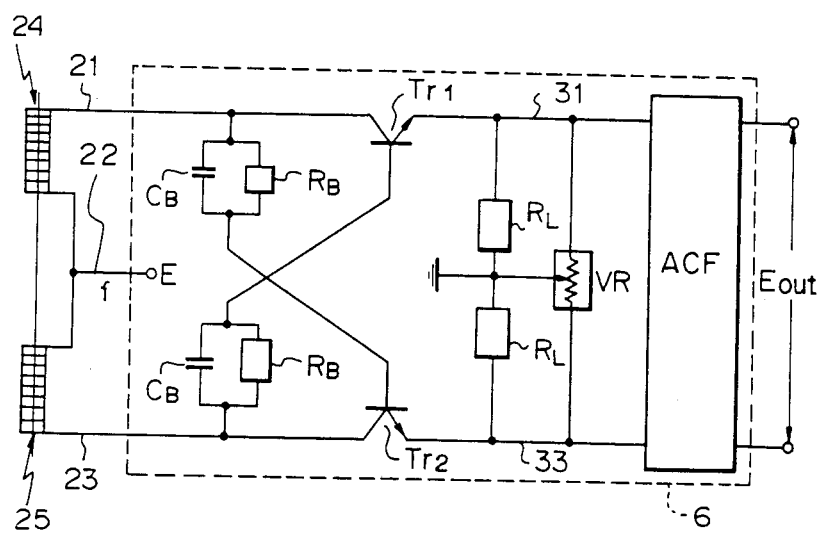
FIG. 4 is a block diagram of a processor of FIG. 1, FIG. 5 and FIG. 6 show experimental curves which show characteristics of the present displacement sensor.

FIG. 4 shows a block diagram of the processor 6, which has an astable multivibrator and an active filter. In FIG. 4, the numerals 24 and 25 are a first inductor group ($L_1$ through $L_{23}$), and a second inductor group ($L_2$ through $L_{24}$), respectively.

The structure of the processor 6 is essentially an astable multivibrator circuit having a pair of transistors $T_{r1}$ and $T_{r2}$, each base of which is coupled with the collector of the other transistor through a parallel circuit of a capacitor $C_B$ and a resistor $R_B$. The collector of the transistor $T_{r1}$ is connected to the lead line 21, and the collector of the transistor $T_{r2}$ is connected to the lead line 23. The emitters of the transistors $T_{r1}$ and $T_{r2}$ are coupled with an active filter ACF through the lines 31 and 33, respectively. Those emitters are bridged by a series circuit of a pair of load resistors $R_L$, and a variable resistors $R_L$. The junction point of said load resistor VR, and the variabler terminal of the variable resistor VR are grounded. The variable resistor VR adjusts the balanced condition of the bridge circuit with two inductance groups (24 and 25) and two resistors ($R_L$) so that no output signal $E_{out}$ is provided when diaphragm 3 does not vibrate. The output of the active filter ACF is the output $E_{out}$ of the processor 6.

The first group of coils 24 and the second group of coils 25 are connected in series so that the differential output of the coils is provided to the lead lines 21 and 23. The junction point of the coils (lead line 22) is coupled with the power source E. The frequency f of the multivibrator is in the range between 100 kHz and 500 kHz, and is preferably 200 kHz. The higher the frequency f is, the more preferable it is, to induce higher voltage. The upper limit of the frequency f is determined by the operational characteristics of amorphous material which the coils consist of.

Preferably, the characteristics of the active filter are adjustable by switching. The active filter may be (1) a low pass filter with the cut-off frequency of 600 Hz, (2) a low-pass filter with the cut-off frequency of 20 Hz, (3) a high-pass filter with the cut-off freqency of 20 Hz, or (4) a bandpass filter which passes DC through 20 Hz or 20 Hz through 600 Hz.

When the two groups of coils 24 and 25 are excited by the signal of the frequency f, the output level $E_{out}$ is zero if the magnetic flux in the inductors $L_1$ through $L_{24}$ by the permanent magnet M is balanced. On the other hand, when the magnetic balance condition is broken, that is, two groups of wires in the coils 24 and 25 are inversely biased with respect to each other with a magnetic field by the permanent magnet M, the inductance of the first group 24 increases, while the inductance of the second group 25 decreases. Therefore, the differential level between the lead lines 21 and 23 is not zero, but has some level except zero relating to the unbalanced condition of the magnetic flux. Thus, the balance condition of the circuit is broken by the movement of the permanent magnet M, and therefore, the output level $E_{out}$ has some amplitude relating to the displacement of the permanent magnet M. A plurality of radially located inductors are used in the present invention because the effect by the earth magnetism to each inductor is cancelled by each other. Therefore, the magnetic flux sensor of the present invention is not influenced by the earth magnetism and/or external magnetic noise.

In operation, the diaphragm 3 is placed on the surface of a chest wall of a body to be inspected, so that the diaphragm 3 vibrates reflecting the vibration of the body surface. The acoustic sound by the vibration of the diaphragm 3 is sent to the ears of a doctor through the empty space 5 and the flexible tube 4.

Simultaneously, the vibration of the diaphragm 3 vibrates the magnet M. The displacement of the vibration of the magnet M causes the generation of the inductance variation in the inductor group 12 (first group 24 and second group 25). In other words, the balanced condition between the first group 24 and the second group 25 is broken, and the differential voltage $E_{out}$ is obtained at the output of the processor 6, which is proportional to the variation of the inductors through the sensor cable 7. The output signal $E_{out}$ is used to display the signal on a screen for visual display, and/or to print the waveforms on a paper.

Next, some experimental results are described.

Figure 5:
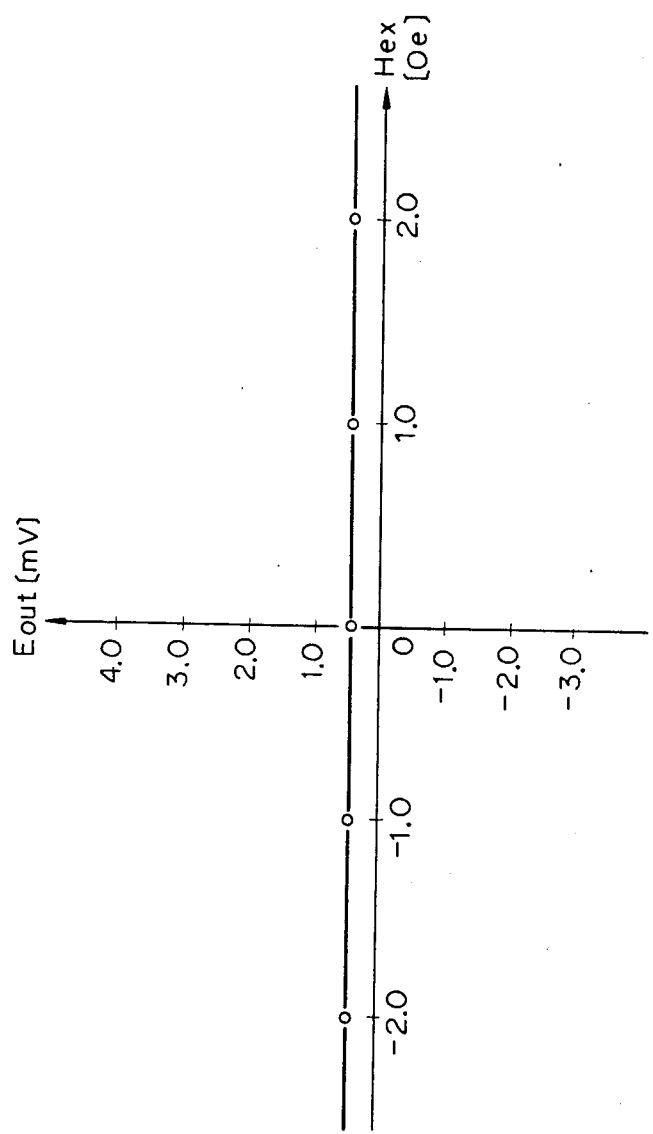
Figure 6:
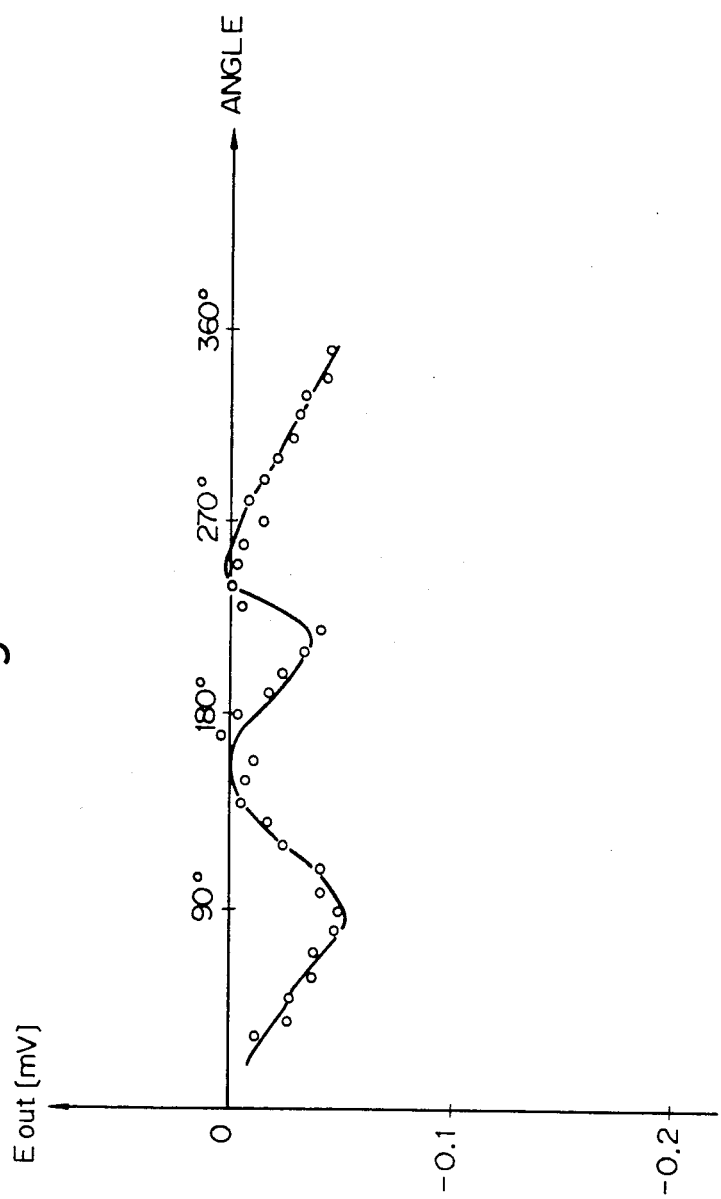

FIGS. 5 and 6 show that the present sensor is not disturbed by external magnetic noise.

FIG. 5 shows curves of output voltage $E_{out}$ when DC (direct current) magnetic flux is roughly perpendicular to the holder plane 11 (FIG. 2). In FIG. 5, the horizontal axis shows the external magnetic field in Oersted, and the vertical axis shows the output voltage $E_{out}$ of the processor 6 in mV. As shown in FIG. 5, the output voltage $E_{out}$ does not change even when the external magnetic field up to $\pm 2$ Oe is applied.

FIG. 6 shows curves of the output voltage $E_{out}$ when the present sensor is rotated in the research laboratory, in which many electric devices generate magnetic noise. In FIG. 6, the length of each coil $L_1$ through $L_{24}$ is 3 mm, the number of turns of each coil is 20, the source voltage E is 2.8 volt, and the sensor is not shielded. The horizontal axis in FIG. 6 shows an angle of the location of the sensor, and the vertical axis shows the output voltage $E_{out}$. As shown in FIG. 6, the fluctuation of the output voltage $E_{out}$ is less than 0.06 mV when the sensor is rotated by 360°. Since normal output voltage $E_{out}$ when the magnet M vibrates is around $\pm 150$ mV, that fluctuation by 0.06 mV is only 0.04%, which is very small.

Next, some cardiograms obtained by using the present stethoscope are described.

Figure 7:
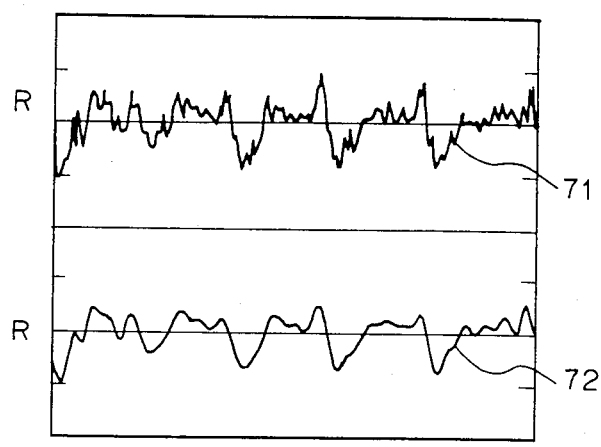
FIG. 7, FIG. 8 and FIG. 9 show curves obtained in a living body using the present displacement sensor.

The curve 71 in FIG. 7 shows total vibration wave in which the sensor is placed on a chest wall of a human body, and the curve 72 shows the heart beat wave which is obtained by deriving the component up to 20 Hz of the curve 71.

Figure 8:
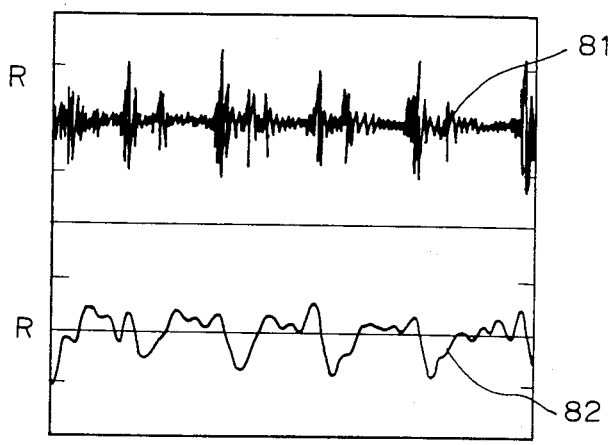

The curve 81 in FIG. 8 is a phonocardiagram which is obtained by using the bandpass filter of 20–600 Hz, and the curve 82 in FIG. 8 is same as 72 for comparing the phase relation between 81 and 82.

Figure 9:
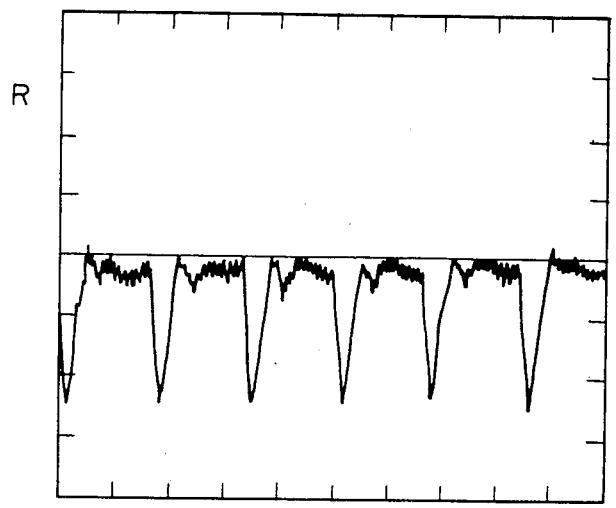
Figure 9B:
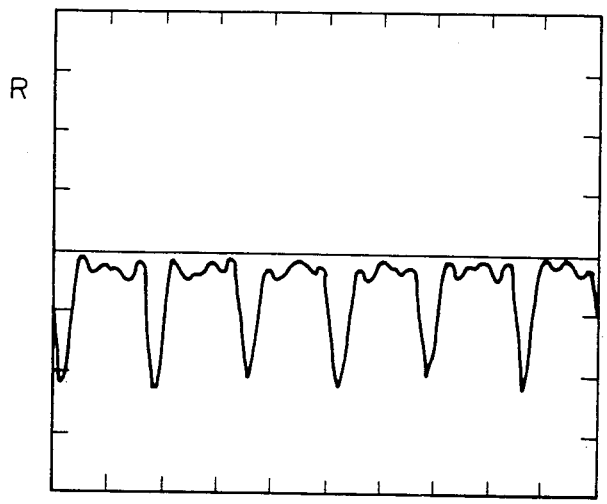

FIG. 9A shows a curve of an artery wave on an elbow, and FIG. 9B is the result of low-pass filtering of the curve of FIG. 9A.

It should be appreciated that the above curves 71 through 82 are free from external noise (earth magnetizm, and/or noise by electric devices), and therefore, the curves are very accurate and reliable. In particular, it should be noted that the present sensor provides the actual movement of a heart, while a prior cardiogram provides only the electrical drive signal of a heart.

Figure 10:
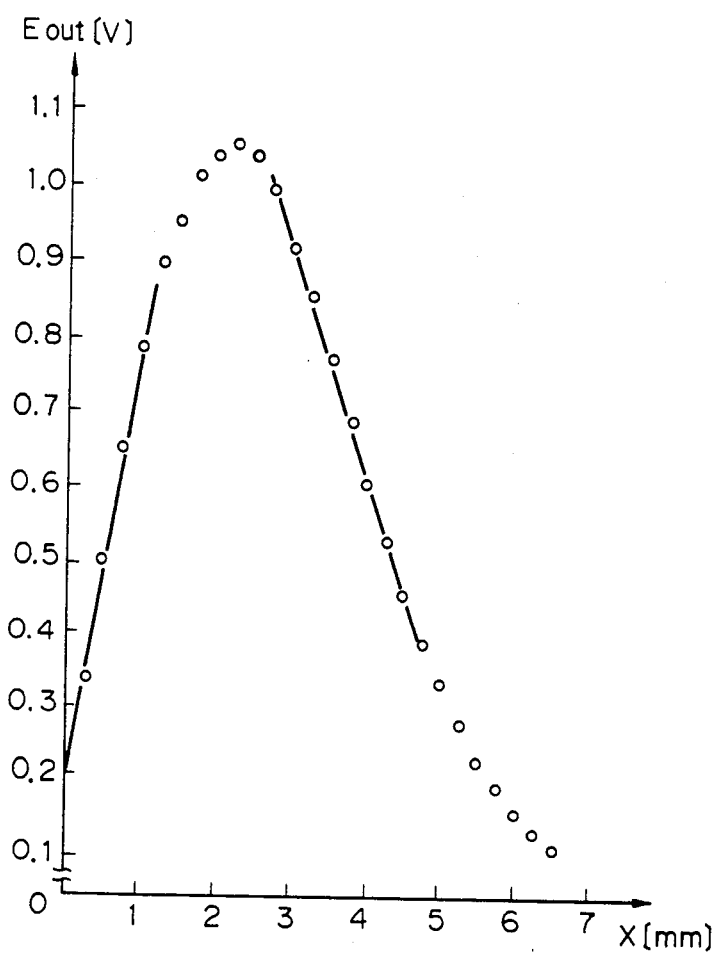
FIG. 10 shows a curve which shows characteristics of the present sensor.

FIG. 10 shows curves between the displacement of the magnet M and the output voltage $E_{out}$. As shown in FIG. 10, there exists a linear portion in the curves, and therefore, it is preferable to use the sensor in the linear portion. In the present embodiment, it is preferable that the sensor is used in the condition that X is between 3 mm and 4.5 mm where X is the length between the end of the magnet M and the plane of the inductors $L_1$ through $L_{24}$. The length X is adjustable by adjusting the screw between the main body 2 and the diaphragm 3.

Some modifications of the present invention are of course possible to those skilled in the art. For instance, although 12 inductors are included in each inductor group 24 and 25, an inductor group having another number of inductors is possible.

Further, a magnetic yoke made of amorphous material may be mounted between the magnet M and the ends of the inductors. That yoke may be located in the holes 13 and 14. That yoke would concentrate the magnetic path of the magnet M, and would decrease the influence by the lateral movement of the magnet M.

Further, another permanent magnet would be located so that the magnetic flux is parallel to the inductors. When the magnetic flux is parallel to the inductors, the sensitivity of the sensor would increase.

As described above in detail, the present stethoscope provides not only an acoustic output but also an electrical output, which may be displayed for visual display and/or printed on a paper. Therefore, an information of auscultation by an expert doctor is obtained on a real time basis. Therefore, the present stethoscope may be used as a training apparatus for new doctors.

When the present apparatus is used as a cardiogram, it is more powerful than a prior one, because the present apparatus provides the actual mechanical movement of a heart, while a prior electrocardiogram provides merely an electrically drive signal to a heart. Conventional mechanocardiograph sensors such as microphones and acceleration transducers are rather difficult to treat due to their bad treatability.

As the present inductor group has many radially located inductors which are connected in series alternately, an external magnetic noise is cancelled in the inductors. Therefore, the present stethoscope can operate accurately with high operational reliability even when the sensor is not protected by a magnetic shield.

From the foregoing, it will now be apparent that a new and improved displacement sensor has been found. It should be understood of course that the embodiments disclosed are merely illustrative and are not intended to limit the scope of the invention. Reference should be made to the appended claims, therefore, rather than the specification as indicating the scope of the invention.

What is claimed is:

1. A displacement sensor comprising:
   a diaphragm which is adapted to be placed on a living body,
   a magnetic pole (M) fixed on said diaphragm,
   a pair of saturable inductors (24,25) positioned close to said magnetic pole,
   each of said saturable inductors (24,25) comprising a plurality of inductors having saturable cores and coils, each coil wound on said core,
   said coils being positioned radially on a plane which is perpendicular to said diaphragm, and
   said coils being connected in series alternately.

2. A displacement sensor according to claim 1, further comprising processor means (6) for supplying alternating signals to said saturable inductors (24,25) to measure inductance of the inductors, thereby reflecting displacement of said magnetic pole.

3. A displacement sensor according to claim 1, further comprising processor means for processing output signals of said inductors.

4. A displacement sensor according to claim 3, wherein said processor means comprises a pair of transistors; a pair of parallel circuits of a capacitor and a resistor coupled between a base of one transistor and a collector of the other transistor, the collector of each transistor being coupled with an end of each inductor (24, 25), a junction point of series connected inductors (24, 25) being coupled with a power supply of frequency f, a balance circuit bridging emitters of said transistors, and a filter coupled across said emitters to provide an output signal.

5. A displacement sensor according to claim 4, wherein said frequency f is in the range between 100 kHz and 500 kHz.

6. A displacement sensor according to claim 4, wherein said filter is a low-pass filter.

7. A displacement sensor according to claim 1, further comprising a hollow tube for coupling acoustically said diaphragm with ears of a user.

8. A displacement sensor according to claim 1, wherein each of said coils is wound on a linear magnetic core made of amorphous material.

9. A displacement sensor according to claim 1, wherein said magnetic pole is a permanent magnet.

10. A displacement sensor according to claim 1, wherein each of said inductors (24, 25) has 12 series connected inductors.

11. A displacement sensor according to claim 1, wherein the length between said diaphragm and said inductors is adjustable.

* * * * *